(12) United States Patent
Baxter et al.

(10) Patent No.: US 11,752,228 B2
(45) Date of Patent: Sep. 12, 2023

(54) HIGHLY EFFICIENT UV C BULB WITH MULTIFACETED FILTER

(71) Applicant: LUMENLABS LLC, Poway, CA (US)

(72) Inventors: Kevin C. Baxter, Tulsa, OK (US); Min Shi, Shanghai (CN)

(73) Assignee: Lumenlabs LLC, Poway, CA (US)

( * ) Notice: Subject to any disclaimer, the term of this patent is extended or adjusted under 35 U.S.C. 154(b) by 0 days.

(21) Appl. No.: 17/160,230

(22) Filed: Jan. 27, 2021

(65) Prior Publication Data
US 2022/0233729 A1    Jul. 28, 2022

(51) Int. Cl.
| | |
|---|---|
| *F21V 7/06* | (2006.01) |
| *A61L 2/24* | (2006.01) |
| *G01C 3/00* | (2006.01) |
| *G01J 1/42* | (2006.01) |
| *A61L 2/10* | (2006.01) |
| *F21V 9/06* | (2018.01) |
| *H01J 61/35* | (2006.01) |
| *H01J 63/00* | (2006.01) |
| *F21Y 115/10* | (2016.01) |

(52) U.S. Cl.
CPC ........ *A61L 2/24* (2013.01); *A61L 2/10* (2013.01); *F21V 7/06* (2013.01); *F21V 9/06* (2013.01); *G01C 3/00* (2013.01); *G01J 1/42* (2013.01); *H01J 61/35* (2013.01); *H01J 63/00* (2013.01); *A61L 2202/11* (2013.01); *A61L 2202/14* (2013.01); *A61L 2202/25* (2013.01); *F21Y 2115/10* (2016.08)

(58) Field of Classification Search
CPC ............... A61L 2/10; F21V 7/06; F21V 9/06
See application file for complete search history.

(56) References Cited

U.S. PATENT DOCUMENTS

| | | | |
|---|---|---|---|
| 3,353,905 | A | 11/1967 | Ellis |
| 5,107,123 | A | 4/1992 | Shi |
| 5,378,896 | A | 1/1995 | Knjaschewitsch et al. |
| 5,387,798 | A | 2/1995 | Funakoshi et al. |
| 6,398,970 | B1 | 6/2002 | Justel et al. |
| 6,437,346 | B1 | 8/2002 | Goudjil |
| 6,793,817 | B2 | 9/2004 | Kuennen et al. |
| 7,198,624 | B2 | 4/2007 | Muzzi et al. |

(Continued)

FOREIGN PATENT DOCUMENTS

| | | |
|---|---|---|
| AU | 2019100806 A4 | 8/2019 |
| CN | 206790749 U | 12/2017 |

(Continued)

OTHER PUBLICATIONS

Buonannoa et al., Germicidal Efficacy and Mammalian Skin Safety of 222-nm UV Light, Aug. 10, 2017. (Year: 2017).*

*Primary Examiner* — Anne M Hines
(74) *Attorney, Agent, or Firm* — Scott Zingerman; James Lea; David Woodral

(57) ABSTRACT

A Far UV C excimer bulb assembly including an excimer bulb, and at least two filters. The excimer bulb emits a path of light in at least two wavelengths. The at least two filters remove all wavelengths of light that are hazardous to human tissue. The at least two filters may each be placed perpendicular to the path of the light generated by the excimer bulb. The at least two filters may be a single, curved or cylindrical filter. The assembly may further include a mirror which may also be curved.

15 Claims, 9 Drawing Sheets

(56) References Cited

U.S. PATENT DOCUMENTS

| | | | |
|---|---|---|---|
| 8,858,886 B1 | 10/2014 | Chuah et al. | |
| 9,214,783 B2 | 12/2015 | Nomura et al. | |
| 10,071,262 B2 | 9/2018 | Randers-Pehrson et al. | |
| 10,780,189 B2 | 9/2020 | Randers-Pehrson et al. | |
| 10,786,586 B2 | 9/2020 | Igarashi | |
| 10,864,287 B2 | 12/2020 | Igarashi | |
| 10,905,790 B1 | 2/2021 | Moore et al. | |
| 10,933,148 B1 | 3/2021 | Patterson et al. | |
| 10,960,094 B1* | 3/2021 | Ismail | A61B 1/0019 |
| 11,007,292 B1 | 5/2021 | Grenon et al. | |
| 2002/0011434 A1 | 1/2002 | Kuennen et al. | |
| 2004/0021420 A1 | 2/2004 | Tsuda et al. | |
| 2004/0239900 A1 | 12/2004 | Aoyama et al. | |
| 2005/0000365 A1 | 1/2005 | Nelsen et al. | |
| 2005/0140292 A1 | 6/2005 | Tiesler-Wittig | |
| 2005/0143793 A1 | 6/2005 | Korman et al. | |
| 2006/0261291 A1* | 11/2006 | Gardner, III | F21V 9/45 250/504 R |
| 2006/0289796 A1 | 12/2006 | Havens et al. | |
| 2007/0154823 A1 | 7/2007 | Marson et al. | |
| 2007/0255266 A1 | 11/2007 | Cumbie et al. | |
| 2008/0224068 A1* | 9/2008 | Mii | H01J 61/307 250/461.1 |
| 2009/0218512 A1 | 9/2009 | Ranta et al. | |
| 2010/0007492 A1 | 1/2010 | Ressler et al. | |
| 2010/0193707 A1 | 8/2010 | Yamada et al. | |
| 2010/0226029 A1 | 9/2010 | Funasaka | |
| 2012/0313014 A1* | 12/2012 | Stibich | H01J 61/00 250/492.1 |
| 2012/0313532 A1* | 12/2012 | Stibich | A61L 2/26 315/150 |
| 2013/0250395 A1 | 9/2013 | Ichimura | |
| 2014/0092238 A1 | 4/2014 | Sandhu et al. | |
| 2014/0116961 A1 | 5/2014 | Bokermann et al. | |
| 2015/0086420 A1 | 3/2015 | Trapani | |
| 2016/0095193 A1 | 3/2016 | Mokhtari et al. | |
| 2016/0195856 A1 | 7/2016 | Spero | |
| 2016/0230939 A1 | 8/2016 | Van Hout | |
| 2016/0317690 A1 | 11/2016 | Dayton | |
| 2017/0095583 A1 | 4/2017 | Stamminger et al. | |
| 2017/0112953 A1 | 4/2017 | Dayton | |
| 2017/0173195 A1 | 6/2017 | Stibich et al. | |
| 2017/0216466 A1 | 8/2017 | Dujowich et al. | |
| 2017/0281812 A1 | 10/2017 | Dobrinsky et al. | |
| 2017/0356602 A1 | 12/2017 | Lin | |
| 2018/0180226 A1* | 6/2018 | Van Bommel | F21K 9/237 |
| 2018/0185533 A1 | 7/2018 | Lalicki et al. | |
| 2018/0264157 A1 | 9/2018 | Benedek et al. | |
| 2018/0296711 A1 | 10/2018 | Brais et al. | |
| 2019/0022260 A1 | 1/2019 | Cole | |
| 2019/0117802 A1 | 4/2019 | Hishinuma et al. | |
| 2019/0160305 A1 | 5/2019 | Randers-Pehrson et al. | |
| 2019/0171111 A1 | 6/2019 | Kimsey-Lin | |
| 2019/0176385 A1 | 6/2019 | Hayakawa et al. | |
| 2019/0192708 A1 | 6/2019 | Igarashi | |
| 2019/0255201 A1 | 8/2019 | Rosen et al. | |
| 2019/0328919 A1* | 10/2019 | Saad | A61L 2/24 |
| 2019/0342942 A1 | 11/2019 | Deros et al. | |
| 2019/0360714 A1 | 11/2019 | Konrad et al. | |
| 2019/0381336 A1 | 12/2019 | Randers-Pehrson et al. | |
| 2019/0388706 A1 | 12/2019 | Randers-Pehrson et al. | |
| 2020/0085984 A1 | 3/2020 | Randers-Pehrson et al. | |
| 2020/0179544 A1 | 6/2020 | Ufkes | |
| 2020/0215214 A1 | 7/2020 | Rosen et al. | |
| 2020/0215215 A1 | 7/2020 | Randers-Pehrson et al. | |
| 2020/0234941 A1 | 7/2020 | Yagyu et al. | |
| 2020/0267810 A1 | 8/2020 | Chemel et al. | |
| 2020/0282086 A1 | 9/2020 | Silverman | |
| 2020/0289686 A1 | 9/2020 | Janik et al. | |
| 2020/0335228 A1 | 10/2020 | Yuan | |
| 2020/0353112 A1 | 11/2020 | Randers-Pehrson et al. | |
| 2020/0397936 A1 | 12/2020 | Deros et al. | |
| 2021/0085810 A1* | 3/2021 | Barron | A61L 2/084 |
| 2021/0158974 A1 | 5/2021 | Seo et al. | |
| 2021/0339183 A1 | 11/2021 | Hourani et al. | |
| 2021/0379215 A1 | 12/2021 | Kelleher et al. | |
| 2021/0386884 A1 | 12/2021 | Brockschmidt, Jr. et al. | |
| 2021/0398230 A1 | 12/2021 | Gupta et al. | |
| 2022/0016297 A1 | 1/2022 | Huang et al. | |

FOREIGN PATENT DOCUMENTS

| | | |
|---|---|---|
| DE | 202020001197 U1 | 5/2000 |
| GB | 2531319 A | 4/2016 |
| GB | 2580838 A | 7/2020 |
| JP | 2010118267 A | 5/2010 |
| JP | 2012109389 A | 6/2012 |
| KR | 100849802 B1 | 7/2008 |
| KR | 1020160127469 A | 11/2016 |
| WO | 2008038548 A1 | 4/2008 |
| WO | 2010001441 A1 | 1/2010 |
| WO | 2014002591 A1 | 1/2014 |
| WO | 2015012592 A1 | 1/2015 |
| WO | 2019190967 A1 | 10/2019 |
| WO | 2020088803 A1 | 5/2020 |

* cited by examiner

Prior Art

HIGHLY EFFICIENT UV C BULB WITH MULTIFACETED FILTER

FIELD OF THE INVENTION

The inventive system is in the field of Ultraviolet Light sanitization, specifically in the C band of wavelengths (UV-C). Such sterilization is presently used in hospital surgery rooms, burn wards, and similar areas that require a high degree of sterilization. The primary difference with these existing uses is the inventive system will be used safely in the presence of people and living tissues.

BACKGROUND OF THE INVENTION

UV-C is recognized as one of the most effective wavelengths at killing the small pathogens because the shorter the wavelength the more powerful it is. Only recently was it discovered that some of the wavelengths in this band are long enough to kill pathogens and short enough to not be able to penetrate stratum corneum (dead skin layer) to harm the living cells underneath. Living cells are many times larger the tiny pathogens that we want to kill. UV-C is from 100 nm to 280 m, and the wavelengths that are generally being considered safe for exposure to human tissue are from 200 nm to 230 nm. UV-C does generate undesirable ozone, especially at wave lengths shorter than 200 nm.

Several studies have shown that hairless mice can be subjected to over 20 times the amount of 200 nm to 230 nm Far UV C as is presently suggested for humans, 8 hours a day, with no adverse effect. These studies have been performed in Japan at University and in the US at Columbia University. These studies are extending in time for up to 60 weeks, still with no adverse effects. Recently humans in Japan were also tested to 250 times the exposure of what is needed to kill 99.9% of pathogens and the test subjects showed no adverse effects, no sunburns, nothing.

There are several technologies that can generate UV light in the germicidal wavelengths, gas-discharge lamps have been around a long time and depending on the gases used can kill pathogens. Low pressure mercury generates 254 nm and has been the standard for decades, it is basically a fluorescent light without the phosphors on the inside that convert the UV to visible light. LEDs have recently been commercialized in the UV-A and UV-B spectrums, but they are very inefficient. There are a few in the longer wavelengths of the UV C spectrum. A research project in Japan recently made an LED that was in lower 200 nm's, the safer portion of the UV-C spectrum, but it was very inefficient and not practical for commercialization anytime soon.

Several companies are making Far UV-C excimer fixtures that emit 222 nm such as Ushio's 12 W Care222, and another by Eden Park's Flat Excimer Lamps. The Ushio fixture has a flat faceplate filter that is separate from the bulb that blocks all unwanted spectrum that the bulb generates, and that spectrum is any wavelength longer than about 237 nm. The Eden Park device has no filter attached at this time and consequently emits 25% of its energy in the dangerous wavelengths from 230 nm to at least 380 nm.

When these filters are not in place then these lights will emit spectrum that is not safe for living tissue. If a maintenance worker were to try and replace a bulb they could be exposed to harmful light. If the glass filter broke or degraded the user would be in danger.

Lastly the materials used are critical. FAR UV-C cannot penetrate plastics and many glasses, only quartz glass can be used without huge losses or downright failure to emit the Far UV-C light. Even oxygen and moisture in the air will also absorb or block the Far UV-C if it is transmitted too far through the air. One additional scientific detail about these filters is that they only allow filtered light that is near perpendicular to the filter's plane. The further the light is from perpendicular to the filter, the greater the attenuation. At 35 degrees from perpendicular there is less than 5% filtered light passing through which means that these flat filters can only form narrow beams of filtered light.

To sanitize large areas with FAR UV C without overexposing portions of those areas or otherwise harming humans would require a very efficient and wide-angle filter and fixture. A wide-angle filter and fixture would allow an even dispersion of sanitizing light, as opposed to fixtures with inefficient narrow beams.

What is needed is a wide-angle UV sanitization light that would be good at killing pathogens with no chance to harm, under any situation, humans that would be present.

SUMMARY OF THE INVENTION

The inventive device provides a human-safe UV-C sanitizing bulb that can be used in continuous public places. The bulb would have a very wide dispersion pattern and would be more efficient than existing Far UV C fixtures. It would be safe in all situations, efficient, affordable, and could monitor itself and report conditions.

Studies at Columbia University show that pass filters tuned from 200 nm-230 nm kill the pathogens and don't hurt humans but the inventive device would use any multi-spectrum far-UVC light source with an integral band pass filter that would block all spectrum with wavelengths longer than 234 nm. This small change to the filtration adds 2.5 times more usable emitted light than the 200-230 nm version and very little emissions in the 230-234 nm range. Ushio has products that filter starting at 237 nm but this risks allowing too much harmful radiation to get through. Ideally the filter material would be deposited directly on the bulb's envelope, which would be made of quartz glass, and this would block all harmful light even when handled during installation or maintenance. The filter material would ideally be very pure hafnium oxide deposited 2~3 um building a cutoff filter 234-400 nm with a depth of approximately 0.0001. This inventive bulb has multiple filters rather than one, multifaceted filters.

The Far UV C bulb emits light in all directions and yet most of this light is absorbed when going through a 200 nm-230 nm filter, even if the bulb has a mirror to reflect most of the light traveling out the back side of the bulb. Mirror losses and light not within the near perpendicular angle dictate that only a small percentage of the light generated is emitted through the filter. The inventive device uses multiple filters, each positioned to be perpendicular to the direction of the light coming from the bulb a distance away from the bulb. The more filters used, and further the distance between filter and bulb, the higher the overall efficiency of the system, and the more even the light output by the filters. As the number of filters goes up to infinite numbers one sees a cylindrical shape take place. A cylinder would be the ideal filter shape with a bulb at the center, all the light emitted would be perpendicular to filter at a given location. This scheme would be many times more efficient than a single flat filter.

The filter of the inventive device could be manufactured directly on the bulb's quartz envelope. This would protect users from UV exposure under all conditions including bulb changing and maintenance.

Not all applications need the inventive device's omnidirectional light, it might be advantageous to emit light at 180 degrees of less. The inventive device could have a bulb that would have a reflector on the backside and an arc shaped filter on the front side where the arc's face is always perpendicular to the light angle coming from the bulb.

The inventive safe bulb would be used in environments where there is regular visible light coming from light fixtures and the inventive bulb could be combined with traditional light sources in a single fixture. If there was any adverse visible color emitting from the UV-C portion of the fixture the visible light's spectrum could be modified and mixed in such a way as to normalize the mixture or average of color coming from the fixture. This type of fixture would ideally be a "can", the type of fixture that is installed in a round hole in a ceiling.

The inventive safe Far UV C system could be packaged as a typical light bulb. The ballast or power supply could be fitted in the base and the bulb would shine omnidirectionally, just like an LED or compact fluorescent light bulb, and it could have conventional lighting included as well.

The foregoing has outlined in broad terms the more important features of the invention disclosed herein so that the detailed description that follows may be more clearly understood, and so that the contribution of the instant inventors to the art may be better appreciated. The instant invention is not limited in its application to the details of the construction and to the arrangements of the components set forth in the following description or illustrated in the drawings. Rather the invention is capable of other embodiments and of being practiced and carried out in various other ways not specifically enumerated herein. Additionally, the disclosure that follows is intended to apply to all alternatives, modifications and equivalents as may be included within the spirit and the scope of the invention as defined by the appended claims. Further, it should be understood that the phraseology and terminology employed herein are for the purpose of description and should not be regarded as limiting, unless the specification specifically so limits the invention.

DETAILED DESCRIPTION OF THE PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processes and manufacturing techniques are omitted so as to not unnecessarily obscure the embodiments herein. The examples used herein are intended merely to facilitate an understanding of ways in which the invention herein may be practiced and to further enable those of skill in the art to practice the embodiments herein. Accordingly, the examples should not be construed as limiting the scope of the claimed invention.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

Figure 1:
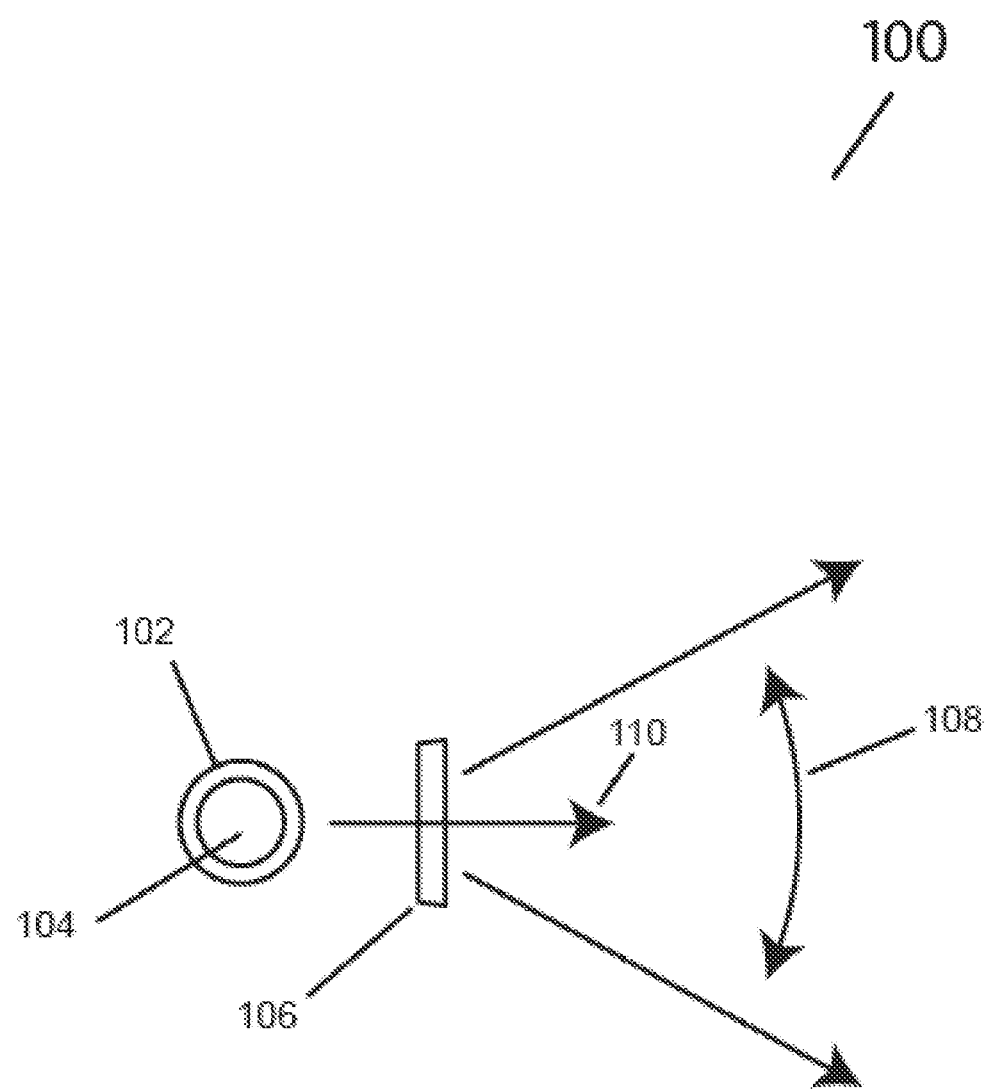
FIG. 1 Simplified view of single filter bulb (prior art)
FIG. 2 Simplified view of single filter bulb with reflector
FIG. 3 Side view of inventive device with 2 filters
FIG. 4 Side view of inventive device with 3 filters
FIG. 5 Side view of inventive device with 4 filters
FIG. 6 Side view of inventive device with cylindrical filter
FIG. 7 Side view of inventive device with arc filter
FIG. 8 View of inventive device with spherical filter
FIG. 9 Side view of cylindrical filter being fabricated in a reactor

Referring now to the drawings, wherein like reference numerals indicate the same parts throughout the several views, in FIG. 1, a representative depiction of an (existing art) filtered Far UV C bulb and filter combination 100. The bulb's envelope 102 contains the excimer gas 104 that when excited generates UV C light in all directions. The bulb 102 shown is round and cylindrical but there are many different common shapes, some are tubes that are flattened with two parallel sides (front and back) and two rounded sides, and some are tubes with a rectangular cross section, to mention a few. From the bulb 102 the light 110 that is generated In a line near to perpendicular to the filter 106 passes through the filter 106 and forms a narrow beam angle (50% of peak) with the field angle 108 (10% of peak) being less than 70 degrees. Generated useful light that is greater than 35 degree from perpendicular to the filter 106 is wasted because it the filter 106 absorbs all of it. This method of generating filtered Far UV C light is very inefficient.

Figure 2:
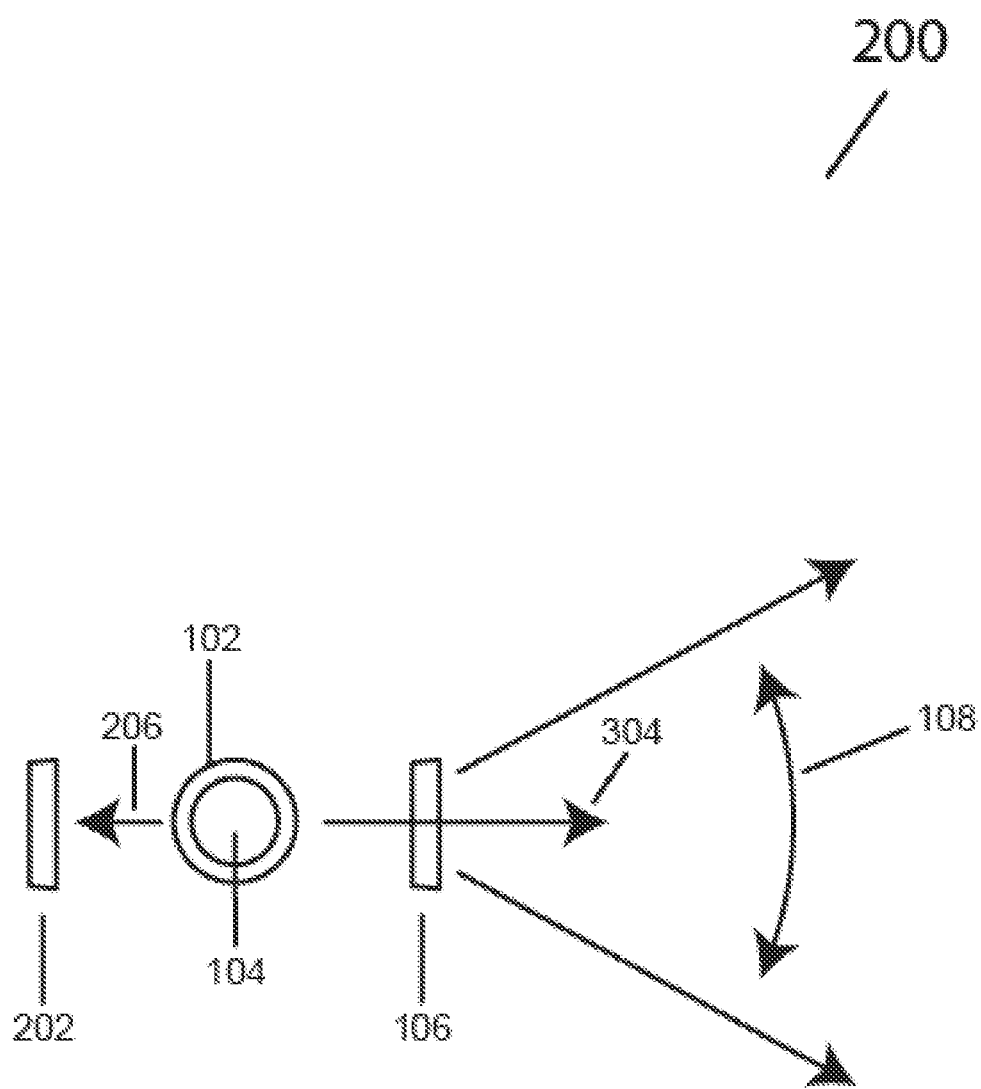

In FIG. 2 shows a depiction of a filtered Far UV C bulb and filter with a back side mirror 200. This filtered Far UV C is method of generating safe Far UV C light is more efficient than was shown in FIG. 1 by almost 70%. The mirror 202 adds a useful path for the light 206 generated of the bulb by bulb 102 that comes out of the back side, it bounces back through the bulb 102 and out the front in addition to the original perpendicular light 304. There are losses in the mirror 202 of about 10% and there are losses through each layer of the bulb's quartz envelope 102, about 10% for each wall, for total losses of about 30%. The mirror 202 is specially processed aluminum to be so efficient, most mirrors or mirrored surfaces would absorb most of the UV C.

Figure 3:
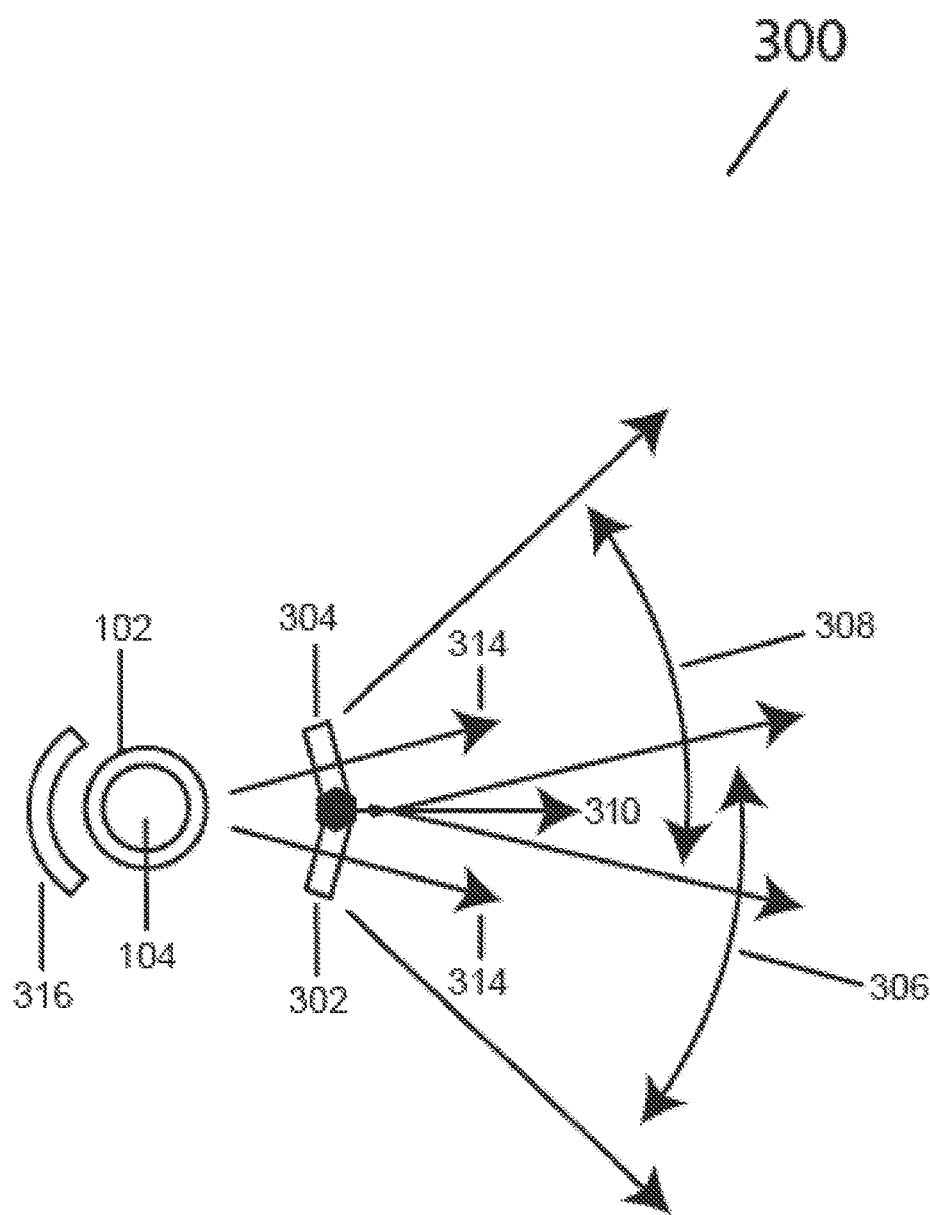

FIG. 3 shows a side section view of the inventive device, a Far UV C bulb with multifaceted filters 300 using 2 filters. The bulb's envelope 102 is the same as in the previously shown examples of FIG. 1 and FIG. 2. The big difference is that there are two filters 302, 304, each is angled to be perpendicular to the angle of the bulb's emitted light 312, 314. The light emitted through each filter 302, 304 separately has a beam, and field 306, 308 angles similar to what was seen in the previous single filter examples FIG. 1, FIG. 2. The filters are connected ideally together using an opaque epoxy 310 to mechanically connect the filters and block light leaks between the filters. This inventive device would ideally have a curved mirror 316 on the back side of the bulb 102 to add 70% to the previous examples. The mirror 316 is shown as a separate part but could be plated onto the bulb's envelope 102 for greater efficiency and lower cost. Each of the 2 filters 302, 304 separately would have the same lumen output as the previous single filter examples FIG. 1, FIG. 2 so this geometry would have twice the total Far UV C output as the single filter versions. Twice the beam and field angles, twice the total delivered Far UV C output using the same power and bulb as before.

Figure 4:
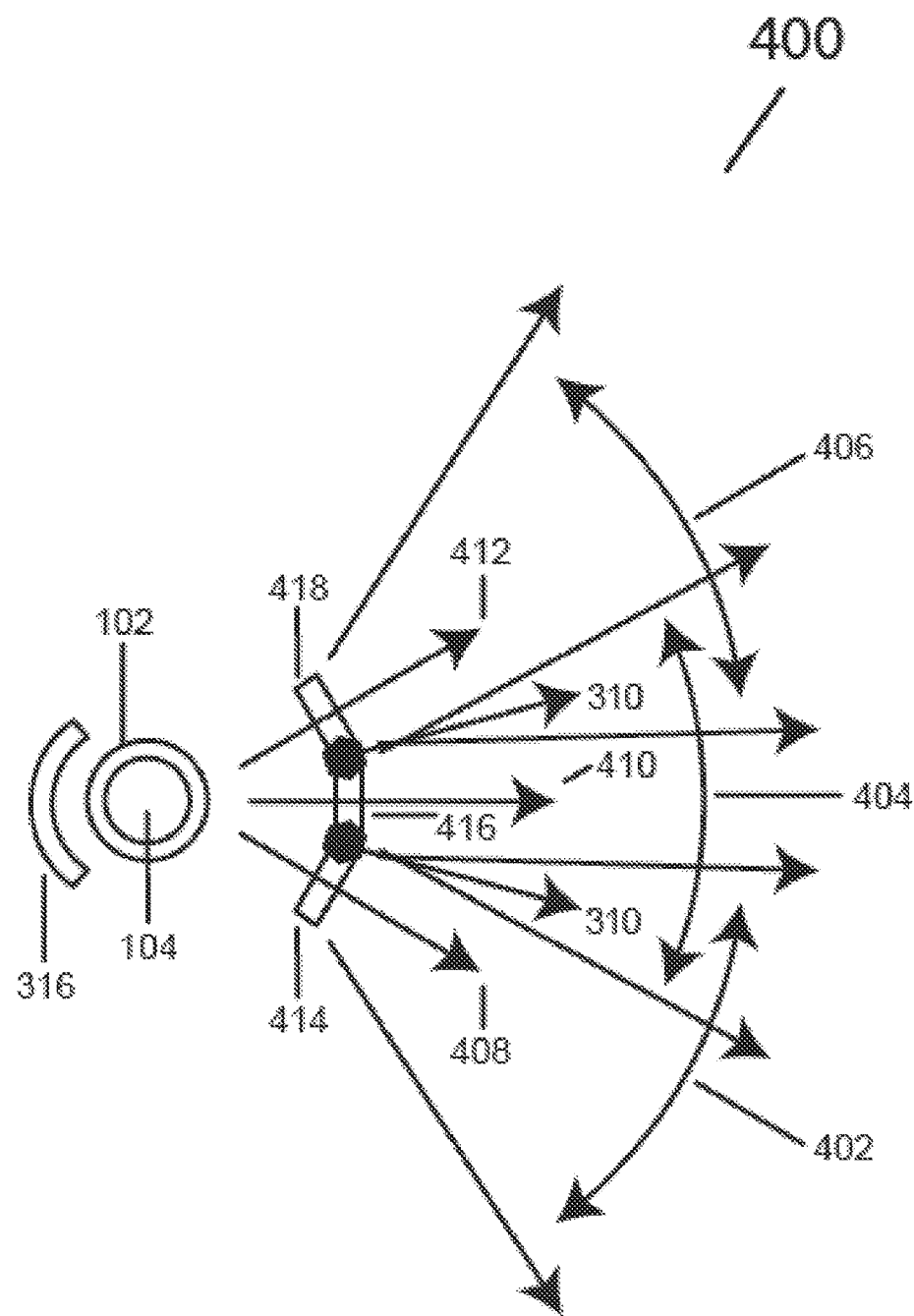

FIG. 4 shows a side section view of the inventive device, a Far UV C bulb with multifaceted filters 400 using 3 filters.

The bulb's envelope 102 is the same as in the previously shown examples of FIG. 1 and FIG. 2. The big difference is that there are three filters 414, 416, 418, each is angled to be perpendicular to the angle of the bulb's emitted light 408, 410, 412. The light emitted through each filter 414, 416, 418 separately has a beam, and field 402, 404, 406 angles similar to what was seen in the previous single filter examples FIG. 1, FIG. 2. The filters are connected ideally together using an opaque epoxy 310 to mechanically connect the filters and block light leaks between the filters. This inventive device would ideally have a curved mirror 316 on the back side of the bulb 102 to add 70% to the previous examples. The mirror 316 is shown as a separate part but could be plated onto the bulb's envelope 102 for greater efficiency and lower cost. Each of the 3 filters 414, 416, 418 separately would have the same Far UV C output as the previous single filter examples FIG. 1, FIG. 2 so this geometry would have three times the total Far UV C output as the single filter versions. Three times the beam and field angles, three times the total delivered lumens using the same power and bulb as before.

Figure 5:
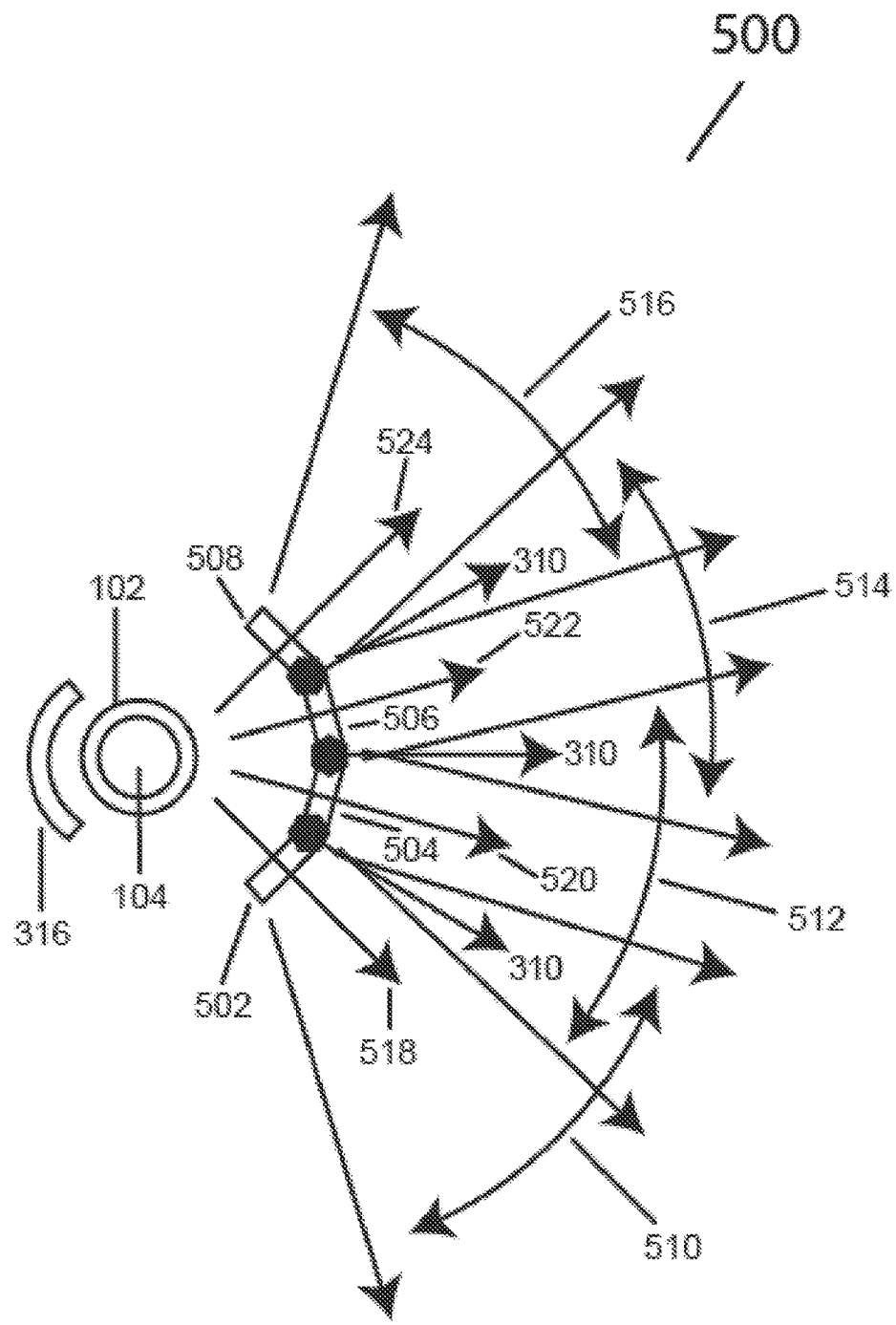

FIG. 5 shows a side section view of the inventive device, a Far UV C bulb with multifaceted filters 500 using 4 filters. The bulb's envelope 102 is the same as in the previously shown examples of FIG. 1 and FIG. 2. The big difference is that there are 4 filters 502, 504, 506, 508, each is angled to be perpendicular to the angle of the bulb's emitted light 518,520,522, 524. The light emitted through each filter 502, 504, 506, 508 separately has a beam, and field 510, 512, 514, 516 angles similar to what was seen in the previous single filter examples FIG. 1, FIG. 2. The filters are connected ideally together using an opaque epoxy 310 to mechanically connect the filters and block light leaks between the filters. This inventive device would ideally have a curved mirror 316 on the back side of the bulb 102 to add 70% to the previous examples. The mirror 316 is shown as a separate part but could be plated onto the bulb's envelope 102 for greater efficiency and lower cost. Each of the 3 filters 502, 504, 506, 508 separately would have the same Far UV C output as the previous single filter examples FIG. 1, FIG. 2 so this geometry would have four times the total Far UV C output as the single filter versions. Four times the beam and field angles, four times the total delivered Far UV C output using the same power and bulb as before. More importantly the beams 510, 512, 514, 516 begin to overlap each other and consequently blend together. This fundamentally changes the nature of the light from a narrow beam single filter fixture into a wide beam and relatively even beam of light that is very efficient.

Figure 6:
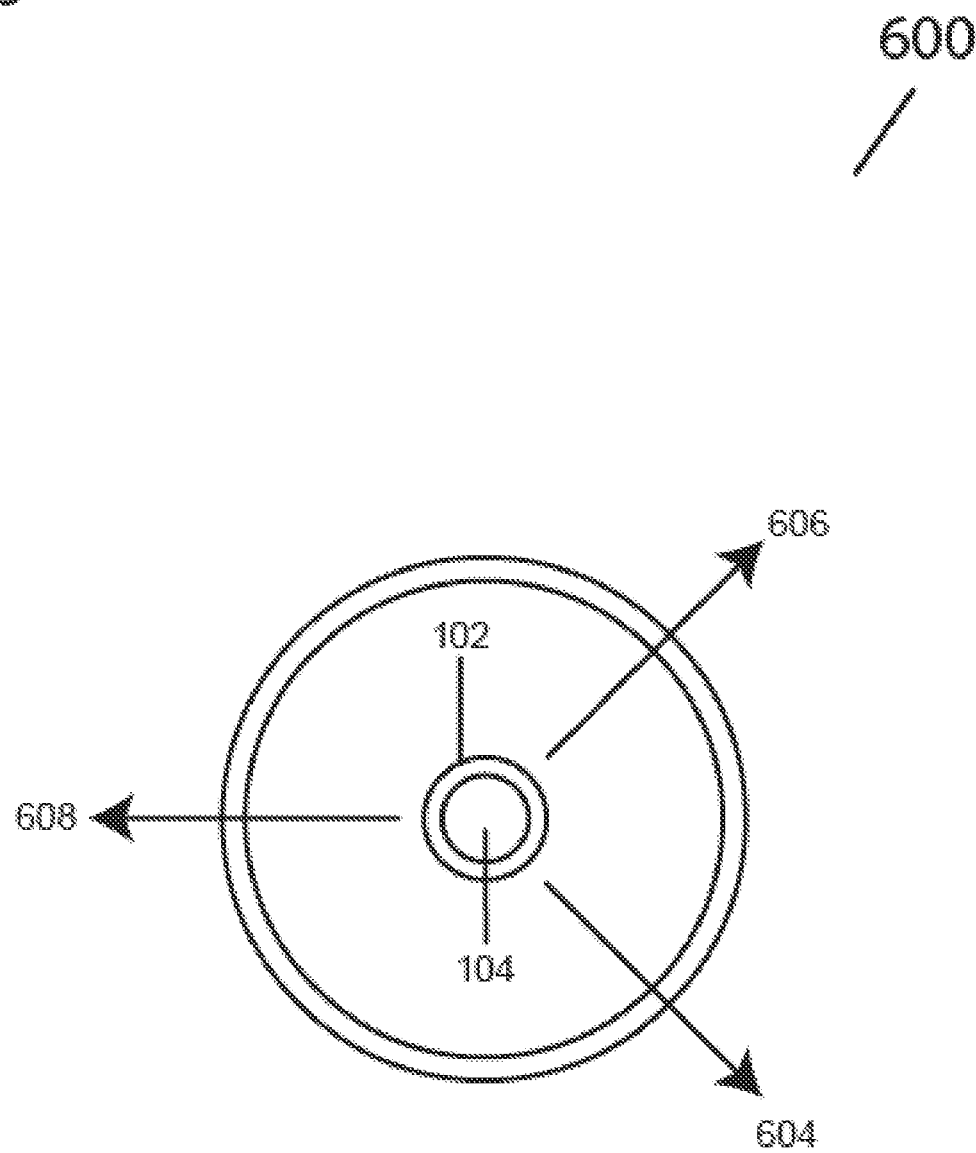

FIG. 6 shows a side section view of the inventive device, a Far UV C bulb with a multifaceted filter 600 using 1 cylindrical filter. The bulb's envelope 102 is the same as in the previously shown examples of FIG. 1 and FIG. 2. The big difference is that the cylindrical filter 602 acts as an infinite number of flat filters with no epoxy joints. Light 604, 606, 608 being emitted from the core 104 of the bulb 102, no matter the angle will always pass perpendicularly through the cylindrical filter 602. There is virtually no generated light that is blocked for not being exactly perpendicular to the filter 602, so there are no losses except for the ends of the cylinder that must be optically sealed off. This inventive device could provide at least ten times more Far UV C than a single flat filter fixture using the same power. Ideally the filter 602 could be directly plated onto the bulb's outer surface 102 for maximum cost savings.

Figure 7:
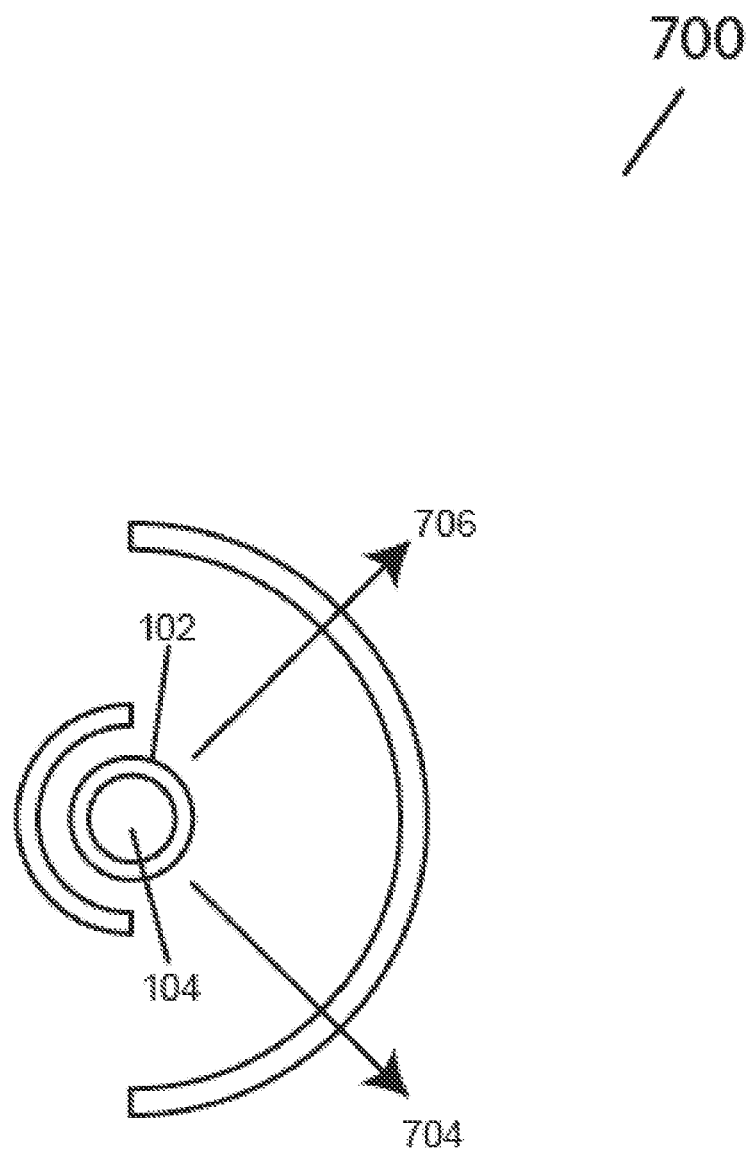

FIG. 7 shows a side section view of the inventive device, a Far UV C bulb with a multifaceted filter 700 using a hemi-cylindrical filter. The bulb's envelope 102 is the same as in the previously shown examples of FIG. 1 and FIG. 2. The big difference is that the cylindrical filter 702 acts as an infinite number of flat filters with no epoxy joints. Light 704, 706 being emitted from the core 104 of the bulb 102, no matter the angle will always pass perpendicularly through the cylindrical filter 702. The inventive bulb and filter combination 700 also has the benefit of a mirror 316 to further boost the light output approximately 70%. This mirror 316 is curved in a semi-cylindrical shape on the backside of the bulb 102. Ideally the mirror 316 would be plated on the backside of the bulb 102. Ideally the filter 702 could plated on the front side of the bulb 102. There is virtually no generated light that is blocked for not being exactly perpendicular to the filter 702, so there are no losses except for the ends of the semi-cylinder filter that must be optically sealed off.

Figure 8:
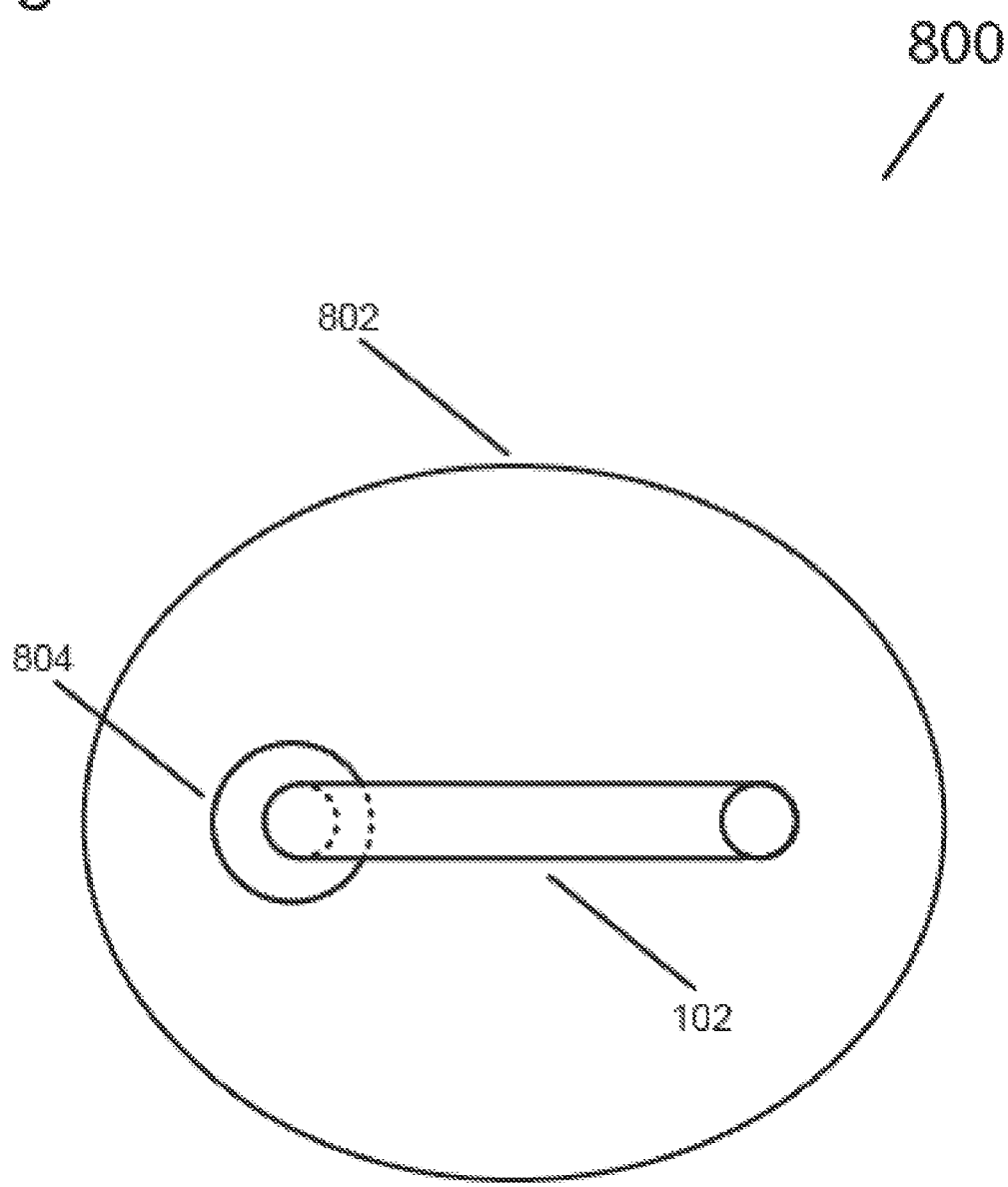

FIG. 8 shows a view of the inventive device, a Far UV C bulb with a multifaceted filter 700 using a spherical filter. The bulb's envelope 102 is the same as in the previously shown examples of FIG. 1 and FIG. 2. The big difference is that the spherical filter 802 acts as an infinite number of flat filters in all 3-dimensional directions for the most efficient far UV C bulb filter combination. Light generated would be at a near perpendicular angle to the filter's face. The only losses are the entry point 804 for the bulb 102.

Figure 9:
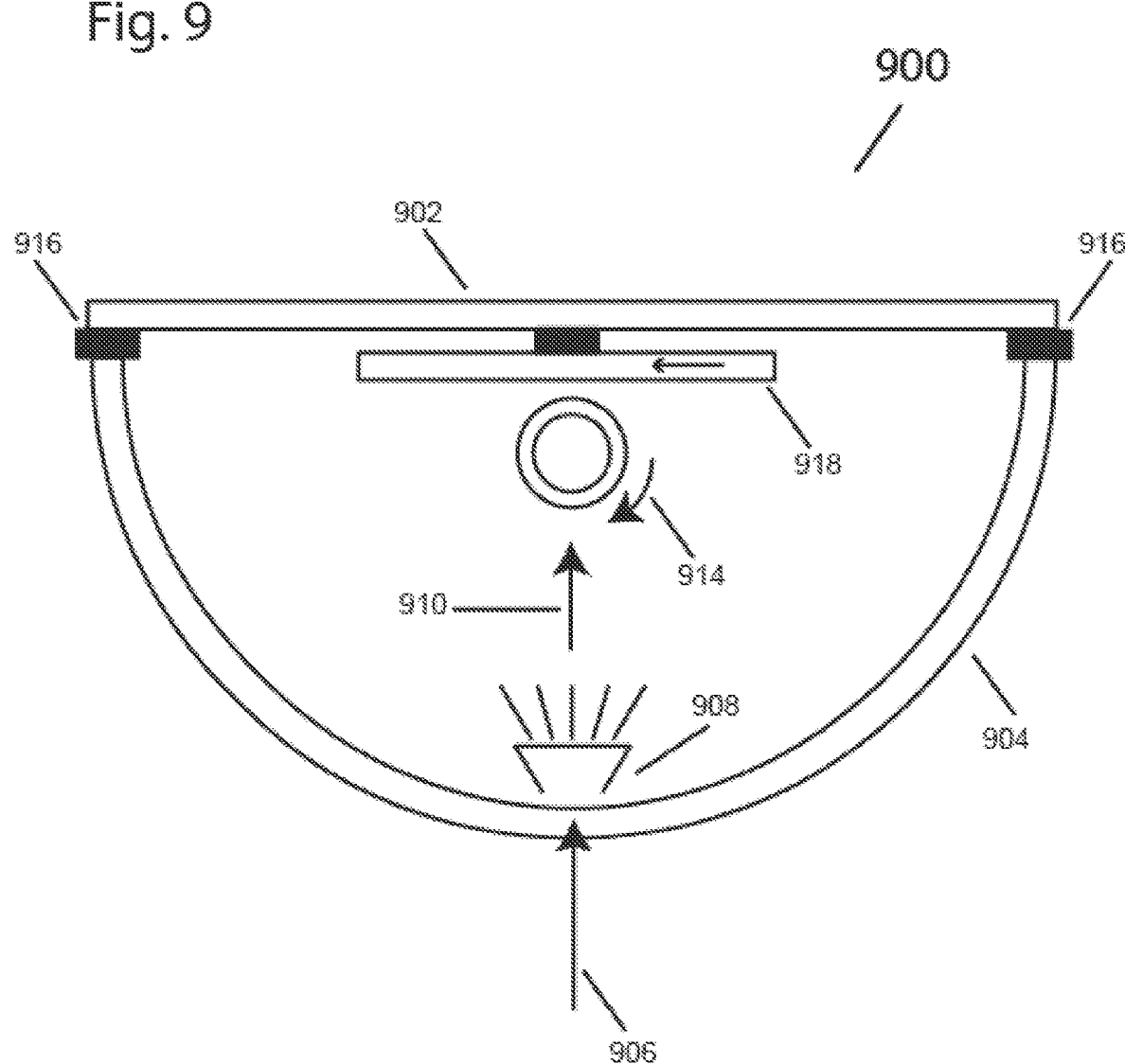

FIG. 9 shows a simplified cross section of a filter-making reactor and a cylindrical filter 900. The lid 902 of a reactor 900 supports an air seal 916 and rotating working platform 918 for filters 912, sort of a motorized lazy-Susan. The lower shell 904 of the reactor 900 holds the gun 908 which ionizes the hafnium wire 906 that is slowly fed in and fogs the chamber's interior in a pseudo plasma state 910 adhering to everything including a filter substrate where it cools. When plating 910 filters onto a substrate, in this case a quartz cylinder 912 the time and amount of hafnium 906 fed determines the thickness of a particular layer. That thickness determines which wavelength(s) of light that layer can block or pass. By very slowly rotating 914 the glass cylinder 912 at a known rate around it long axis by mechanical means would be a further variable in the layer thickness equation. The rotation 914 would allow a relatively even layer of hafnium 910 all of the way around the cylinder 912. The cylinder 912 could also be the bulb 102 where the outer surface of the bulb 102 is plated with hafnium 910 to become the filter 912 as well. Approximately 100 layers are required for an ideal Far UV C filter. For simplicity the above explanation does not mention the voltages, temperatures, vacuum, gases, time, pressure, or monitoring equipment needed for properly operating a filter reactor, these elements are well known to those skilled in the art. Only the pertinent, unique, and inventive elements have been discussed.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. A Far UV C excimer bulb assembly, comprising;
   an excimer bulb which generates beams of light in a plurality of wavelengths substantially comprising far UV C;
   at least two filters, wherein said at least two filters are hafnium based filters;
   said at least two filters are external to and separated from said excimer bulb;
   said at least two filters each having a cut-off wavelength of 234 nm so as to block substantially all UV C wavelengths longer than 234 nm emitted from said excimer bulb; and,
   said at least two filters are each oriented perpendicular to a path of the beams of light such that a majority of the light strikes them with an incidence angle of zero degrees.

2. The Far UV C excimer bulb assembly of claim 1 where the said at least two filters are three (3) filters.

3. The Far UV C excimer bulb assembly of claim 1 where the said at least two filters are four (4) filters.

4. The Far UV C excimer bulb assembly of claim 1 further including a mirror external to said excimer bulb.

5. The Far UV C excimer bulb assembly of claim 4 wherein said mirror is curved.

6. The Far UV C excimer bulb assembly of claim 4 wherein said excimer bulb includes an exterior surface and said mirror is plated on said exterior surface of said excimer bulb.

7. The Far UV C excimer bulb assembly of claim 1 wherein said excimer bulb has a translucent face.

8. A Far UV C excimer bulb assembly, comprising:
   an excimer bulb which emits far UV C wavelengths of light;
   a curved filter external to and separated from said excimer bulb, said curved filter including an arc;
   said curved filter being hafnium based;
   said curved filter having a cut-off wavelength of 234 nm such that substantially all far UV C wavelengths of light shorter than 234 nm pass through said curved filter and said curved filter blocks substantially all wavelengths of UV C light longer than 234 nm;
   said excimer bulb positioned at least partially and centered within said arc so that a majority of said safe-far UV C wavelengths of light pass perpendicularly through said curved filter.

9. The Far UV C excimer bulb assembly of claim 8 wherein said curved filter is a cylinder surrounding said excimer bulb and said excimer bulb is positioned at the center of said cylinder.

10. The Far UV C excimer bulb assembly of claim 8 wherein said curved filter is a semi-cylinder.

11. The Far UV C excimer bulb assembly of claim 10 further includes a mirror external to said excimer bulb.

12. The Far UV C excimer bulb assembly of claim 11 wherein said mirror is curved.

13. The Far UV C excimer bulb assembly of claim 11 where said excimer bulb includes an exterior surface and said mirror is plated on said exterior surface of said excimer bulb.

14. The Far UV C excimer bulb assembly of claim 8 wherein said selected far UV C wavelengths of light which pass perpendicularly through said curved filter are shorter than 234 nm.

15. The Far UV C excimer bulb assembly of claim 8 wherein said excimer bulb has a translucent face.

* * * * *